(12) United States Patent
Rashid (10) Patent No.: US 7,754,938 B2
(45) Date of Patent: Jul. 13, 2010

(54) OLFACTORY PATCH

(76) Inventor: Asrar Rashid, 23, Ranelagh Grove, Nottingham, Nottinghamshire (GB) NG8 1HR ( * ) Notice: Subject to any disclaimer, the term of this patent is extended or adjusted under 35 U.S.C. 154(b) by 0 days.

(21) Appl. No.: 11/430,098

(22) Filed: May 9, 2006

(65) Prior Publication Data

US 2007/0055216 A1    Mar. 8, 2007

(51) Int. Cl.
*A61F 13/15*    (2006.01)
*A24F 25/00*    (2006.01)
*B65D 25/08*    (2006.01)
*B65D 69/00*    (2006.01)

(52) U.S. Cl. .......................... 604/359; 239/34; 239/36; 206/221; 206/229

(58) Field of Classification Search .................. 604/359; 239/6, 34, 36, 56; 206/221, 229
See application file for complete search history.

(56) References Cited

U.S. PATENT DOCUMENTS

| | | | | | |
|---|---|---|---|---|---|
| 4,277,024 A | * | 7/1981 | Spector | ........................ | 239/36 |
| 4,327,056 A | * | 4/1982 | Gaiser | ........................ | 422/124 |
| 5,782,408 A | * | 7/1998 | Carter | ........................ | 239/34 |
| 6,162,454 A | * | 12/2000 | Ahr et al. | .................... | 424/411 |

* cited by examiner

*Primary Examiner*—Jacqueline F. Stephens
(74) *Attorney, Agent, or Firm*—The Ronald Law Group, LLC; Carl A. Ronald (57) ABSTRACT

An olfactory patch comprises a well formed by a reservoir layer, the well is sandwiched between a barrier layer and a permeable layer. The permeable layer defines a pathway for olfactory fluid flow from the well. The flow of the olfactory fluid may be commenced by an initiator mechanism. The olfactory patch may utilize any olfactory fluid or combination of fluids within the same patch. The patch may utilize olfactory fluid which provides aromas or masks odors or has deodorizing capability or the olfactory fluid may contain therapeutic or pest control agents which are released from the patch by aromatization or by direct skin absorption or by inhalation.

20 Claims, 3 Drawing Sheets

OLFACTORY PATCH

CROSS-REFERENCE TO RELATED APPLICATIONS

GB 0518253.0

FEDERALLY SPONSORED RESEARCH

Not applicable

SEQUENCE LISTING OR PROGRAM

Not applicable

BACKGROUND OF THE INVENTION

1. Field of Invention

The present invention relates to olfactory patches used to disseminate olfactory. Specifically, the olfactory may have various uses such as to provide fragrance, odours, or to have deodorising capability or be of therapeutic value.

2. Background of the Invention

It will be understood that it is inherent with human beings perspiring that they will create bodily odours, which are not pleasant. Traditionally these odours have been masked with deodorants and fragrant body sprays such as perfumes as well as by provision of anti perspirant agents to reduce the perspiration causing the body odours. Applying an amount of fragrance directly to the skin at a level to produce a desired effect is only short-lasting. Nevertheless, it will be appreciated that perspiration builds over the course of the day and certain individuals perspire more than others. In such circumstances it is difficult to provide deodorants and fragrances which are applicable to every individual and that have an extended period of action.

Traditional anti perspirants and deodorants comprise sprays or roll-on fluids and gels which are applied directly to the skin. Thus, there is the potential for allergic reactions with such direct contact. It will also be understood that the potential for controlled release of olfactory agents to mask bodily odours is difficult. Aerosol type anti perspirants and deodorants may not be environmentally friendly due to their propellant gas.

Medicinal patches have been used to provide the topical application of a therapeutic agent or agents, which are absorbed through the user's skin. It is appreciated that, similar to the fragrance patches, these patches will have a limited period of action, the action is terminated when the agent is depleted from the emitting layer. Depleted medicinal patches must be replaced by the user for a sustained release of medication to cause a desired clinical effect and therefore to be of benefit to the user.

Prior art has shown some attempts at a solution to the problems mentioned. U.S. Pat. No. 4,880,690 of Szycher et al. describes a multi-layer perfume patch member for timed release of fragrance. It is intended that the user adhere this patch to the skin by a layer of pressure sensitive adhesive to emit a desired level of fragrance outwardly away from the skin of the user and directly from the perfume patch, over an extended period by a controlled time-release mechanism. The release of the fragrance is functional upon the constituents of the emitting membrane; thereby changing the nature of the olfactory would require the production of a fragrance emitting-layer that is tailored to specific requirements utilizing in-situ polymerisation techniques in the production process. Olfactory's with differing physical properties may require complex changes in membrane characteristics and constituents to match the function desired.

U.S. Pat. No. 6,162,457 describes a user-worn fragrance patch; here the fragrance emitting side is against the skin of the user allowing for the escape of olfactory. However this device is dependant on the amount of olfactory that is deposited onto the fragrance-emitting layer. Clearly the period of action is limited by the amount of fragrance within this fragrance-emitting layer. The effectiveness of the patch is focused on the characteristics of the fragrance-emitting layer and not on the specifics of the olfactory. An initiator mechanism for when the user wishes for the patch to start release of olfactory is not built into the patch and there is no reservoir, so once the olfactory is deplete, more olfactory needs to be deposited onto the surface.

WO Patent 2004/075933 A3 details a composition of membranes of differing constituents that are made of fragrant material, barrier layers and active layers. This method utilizes the production of differing membranes with the inherent capacity to function so that the patch can emit olfactory or pharmacologically active compounds. Similarly this process utilizes a complex polymerisation technique in the constitution of an active layer and the fixing of additional layers to take into consideration the physical characteristics of the olfactory and desired function. Further 2004/075933 does not utilise a reservoir as the active substance is embedded within the active membrane. Therefore introducing new olfactory would require a chemical process of constitution. Further, once the active agent is depleted from the active membrane, the same membrane cannot be refilled.

Spector U.S. Pat. No. 4,277,024 teaches an olfactory patch compromising a well formed by a reservoir layer sandwiched between a barrier layer and a permeable layer from olfactory in the well. Ahr et al U.S. Pat. No. 6,162,454 teaches an olfactory patch comprising a well formed by a reservoir layer sandwiched between a barrier layer and a permeable layer and the patch is capable of being placed onto various surfaces. Further prior art Carter U.S. Pat. No. 5,782,408 teaches a scent pad where body heat from the user increases the rate of scent diffusion. However prior art does not describe an initiator mechanism that would release the olfactory from within the product. This is due to the fact that the prior art describes olfactory that is within the membrane of the emitting layer and is not held within a reservoir well. Alternatively, the user is asked to spray fragrance onto the patch surface itself. In this case the release of olfactory has onset from the time of deposition by the user and there is an expiration time that is determined by depletion of olfactory from the emitting layer. The amount of olfactory that can be contained within a given area of emitting layer is less than if the emitting layer was associated with a reservoir that drained into the emitting layer once a breach was initiated with the reservoir well.

More recently sophisticated but expensive electronic release devices in the form of olfactory patches have been known. These olfactory patches comprise reservoirs of liquid olfactory perfumes or otherwise which are pumped and released by small electronic devices as required and in accordance with the user's needs. As indicated these devices are expensive and tend to be relatively thick. Furthermore in view of the expense of the device, it is desirable to provide relatively large olfactory reservoirs and means for recharging of the olfactory patch rather than simple disposal.

It would be desirable to provide a patch for releasing volatile substances over an extended period of time. Also it is desirable; where the olfactory agents are active and of potentially medicinal value that the exposure to the user's skin should be limited. Further, in certain cases it may be desirable for a certain drug or group of drugs to have a localised action locally, either topically or by inhalation, which could be achieved by utilising an olfactory patch mechanism.

OBJECTS AND ADVANTAGES

Accordingly, several objects and advantages of my invention are described. Most importantly the olfactory utilizes a reservoir system to provide a supply of olfactory to the releasing area once the reservoir is breached by an initiator mechanism. The concentration of olfactory at the releasing area is dependant upon the flow of olfactory from a reservoir, which thereby provides a steady supply of olfactory to meet demand. Thereby the patch can function over an extended period of time. The use of an initiator mechanism allows the user to determine requirements, rather than allowing the membrane to diffuse out all olfactory and therefore become depleted.

In a further advantage, differing olfactory's may be mixed, or separate olfactory's could be used within a sole patch, thereby one olfactory patch may have multiple functionality, e.g. releasing perfume and deodorizing.

It is appreciated that olfactory differ physically depending upon their constituents and their functionality. Such physical differences can be catered for by changing the design of the olfactory pathway within the olfactory patch. For example the diameter of holes within the emitting membrane can be changed according to the desired diffusion characteristics of the olfactory. Changing the physical structure of the olfactory will be much easier than redesigning membrane constituents that are impregnated within membranes. Therefore there is flexibility regarding the design of the patch, as the functionality is less reliant on the characteristics of various membranes, as most of the membranes with the olfactory system are inert. Thereby the patch can deliver substances which differ greatly in physical characteristics, such as fragrances, masking odours, or deodorising agents or therapeutic agents.

In another advantage, the olfactory has within it olfactory flow that is in the direction from a reservoir, outwards, through the patch. This flow olfactory will deplete the reservoir, but the reservoir can be easily refilled or be renewed by virtue of ease of accessibility to the reservoir.

In another advantage, the olfactory patch will be of particular benefit in administering therapeutic agents. The olfactory patch can be used for drug delivery, whether the olfactory drug requires aromatisation and inhalation or whether the olfactory is required to be absorbed through the skin. The advantages of the olfactory patch in terms of drug delivery is that the patch system can be used to provide a given amount of medication at a certain dose range, to whatever site is required. It will be understood that it is usual for drugs that are administered topically compared to systemically to be associated with lower toxicity for the user. This may be of particular use for pain medication where the patch could be applied to a specific area, such as the site of pain. It will be appreciated that often topical or inhaled drug delivery may be more favourable compared to when a drug is given orally or intravenously.

Another advantage of the patch system is that an initiator mechanism is incorporated into the patch. The initiator mechanism is utilised to control the flow of the olfactory. This may be particularly useful in situations where the olfactory has therapeutic benefit. Medicines also applied to the skin may need to be released in a time dependant fashion determined by the characteristics of olfactory flow. Such designs would help to avoid toxicity to the user. The reservoir characteristics would allow for time extended administration of drugs, over an extended period of time. Thus the user may be administered lower doses of drugs over the long-term as the levels are maintained at a therapeutically active range without major variations in serum concentrations. For example, pain relief to the knee it would be desirable to have a sustained release patch to that area.

It is yet another object of the present invention to improve over the disadvantages of the prior art. Further objects and advantages of my invention will become apparent from a consideration of the drawings and ensuing description.

SUMMARY OF THE INVENTION

In keeping with these objects a generic olfactory patch is described for multiple uses such as release of fragrance, for deodorization, or to have therapeutic functionality through inhalation or topical absorption through skin of medicinal agents. The functionality and design of the patch is responsible for the extended time of release of olfactory from the patch.

DETAILED DESCRIPTION OF THE INVENTION

In accordance with the present invention there is provided an olfactory patch comprises a well formed by a reservoir layer, the well sandwiched between a barrier layer on a top side and a permeable layer on the bottom side, the permeable layer defining a pathway for an olfactory fluid flow from an olfactory fluid held in the well. The well wall must be breached by an initiator mechanism to commence olfactory flow.

Preferably, the pathway is radial. Alternatively, the pathway is vertical or lateral from one side of the patch to the other.

Generally, the pathway has a preferential bias for radial flow or movement along the pathway. Typically the olfactory fluid flow is by diffusion from a high concentration to a lower concentration of fluid in the periphery of the permeable layer. The olfactory fluid is radiated or convectively released.

Typically, the pathway is defined between the reservoir layer and a surface upon which the permeable layer is secured in use. Typically the permeable layer is secured by adhesion. Normally, an adhesive layer is applied upon the bottom of the permeable layer to provide adhesion. Typically such adhesion is to human skin. Possibly, the adhesive layer provides an impermeable base for the permeable layer further continuing the radial pathway between the adhesive layer and the reservoir layer.

Generally, the permeable layer comprises a paper matrix. Possibly, the paper matrix has a consistency typical of a filter paper.

Normally, the permeable layer extends laterally beyond the reservoir layer.

Possibly, the permeable layer is actively exposed by displacement or removal of a masking screen.

Normally, the reservoir is filled with a reservoir matrix.

Typically, the reservoir matrix is a non woven fabric. Generally, the non woven fabric is cotton wool. Normally, the permeable layer preferentially draws the olfactory fluid flow in use from the well.

Advantageously, the well has a conical cross-section narrowing towards the permeable layer. Generally, the well is in contact with the permeable layer at a central position within the reservoir layer.

Advantageously the patch is compressible to initiate or stimulate olfactory flow along the preferential pathway. Preferably, compress is applied upon the barrier layer Generally, the reservoir comprises a membrane rupturable by compression. Possibly, the membrane divides the well. Possibly, the membrane divides the well vertically. Alternatively, the membrane divides the well laterally. Advantageously the membrane encapsulates the well to inhibit olfactory release.

Possibly, the membrane is associated with initiators to facilitate rupture upon compression. Normally, the initiatory are spikes.

Possibly the patch is secured to a pillow or bed sheet or clothing or bedding or footwear or packaging.

Typically, the reservoir contains a perfume or a mosquito repellent or a decongestant or other olfactory, or two or more of these or combination of these.

Possibly, the permeable membrane is relatively expansive to provide a printing or writing area about the reservoir layer.

Generally the reservoir layer is at least impermeable upon a base surface in contact with the permeable layer about an opening to the well.

Generally the permeable layer is directly below the reservoir layer has an impermeable surface secured to it. Normally, the impermeable surface is upon the permeable layer not in contact with the contact layer.

Possibly, the barrier layer can be penetrated to fill the well with an olfactory source. Possibly, the barrier layer is self-sealing after penetration to fill the well. Advantageously the barrier layer is penetrable through a gland or one-way valve joint in the barrier layer to which a nozzle to fill the well can be secured.

Generally in combination the barrier layer, the reservoir layer and the permeable layer when secured together have a thickness of less than 5 mm and preferably less than 3 mm.

Also in accordance with the present invention there is provided an olfactory combination comprising an olfactory patch as described above, and an olfactory vessel comprising a coupling for penetration or joining with a reciprocally shaped part of the barrier layer to define a pathway for olfactory passage to the reservoir.

Typically, the coupling is a needle. Alternatively, the coupling is a nozzle. Advantageously, the vessel is a compressible bottle to allow olfactory within the vessel to be forced through the coupling into the well.

Further in accordance with the present invention there is provided an assembly of olfactory patches as described above in a stack.

Embodiments of the present invention will now be described by way of example and with reference to the accompanying drawings in which:—

The use of deodorants and olfactories in order to mask body odours or create pleasant odours for suboptimal association is well known. Directly applied roll-on deodorants and sprays have limitations with respect to their usage and may stain clothing or otherwise. Alternate use of impregnated patches have problems with respect to sustained release mechanisms whether that be through impregnation into a receptor fabric or otherwise through use of relatively expensive micro electronic mixing approaches. It will be understood that price is an important factor with respect to the acceptability of an olfactory odour providing system, but that system must be sufficiently sophisticated to allow increases or decreases in the amount of olfactory released and provide sufficient flexibly with regard to use.

The present olfactory patch utilises a permeable layer which generally extends laterally. The olfactory patch has a large release area in order to regulate flow of the olfactory. The olfactory is normally in the form of the fluid and is drawn by diffusion from a central well laterally and radially along a preferred pathway for release from the exposed parts of the permeable layer. Fluid flow to the permeable layer from the well occurs on initiation of a mechanism that causes the breach of an impermeable membrane that encloses the opening of the well.

Figure 1:
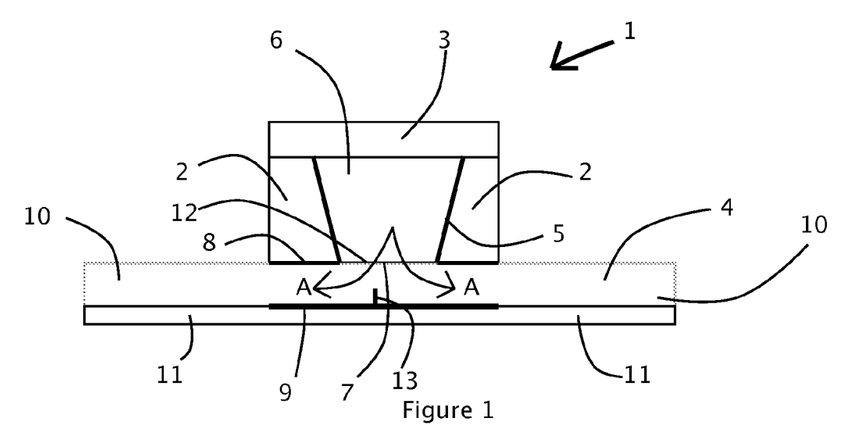
FIG. 1 is a schematic cross section of a first embodiment of an olfactory patch in accordance with the present invention.

Referring to FIG. 1 illustrating a first embodiment of an olfactory patch in accordance with the present invention it will be noted that the patch 1 comprises a reservoir layer 2 substantially sandwiched between a barrier layer 3 and a permeable layer 4. The reservoir layer 2 incorporates a recess 5 which defines a well 6 within which normally a reservoir for stabilised release of olfactory is located. Generally the reservoir layer 2 is impermeable such that an olfactory in the form of a liquid or gel in the well 6 is retained and presented upon the permeable layer 4 at a central opening 7. Lining the central opening of the well is a membrane 12 which is ruptured by an initiator mechanism such as by squeezing the upper or lower side of the olfactory patch so that a fine pin 13 that is attached internally to the underside of the patch 9 ruptures the membrane 12 allowing the flow of olfactory from the well.

As indicated the well 6 generally incorporates a reservoir matrix such as a non woven fabric or cotton wool. Thus, the olfactory is drawn by diffusion along the permeable layer 4 in the direction of arrowheads A. The matrix ensures that the well 6 does not collapse as olfactory is removed. However, if the barrier layer is sufficiently elastic and flaccid as well as the walls of the reservoir layer 2 then such collapse may not act to retard the flow in direction of arrowheads A.

It will be understood that for measured release of olfactory the rate of flow in the direction of arrow heads A is regulated by the diffusion gradient between the reservoir, when a matrix layer is present and the permeable layer. This diffusion gradient is defined by the materials used and their relative dimensions.

The barrier layer 3 generally comprises an impermeable material to ensure that the reservoir 6 is effectively isolated and so that the olfactory only passes through the opening 7 to the permeable layer 4.

The permeable layer 4 is arranged to create a preferential path for the olfactory. This path is generally radial and provided between a bottom surface 8 of the reservoir layer 2 and a surface upon which the patch 1 is secured. It will be appreciated that normally the patch 1 will be rectangular or circular or oval such that the olfactory passes along the path defined by the permeable layer 4 to the exposed surfaces 10. These exposed surfaces 10 may utilise body heat in order to facilitate vaporisation and release of the olfactory.

It will be understood that the present patch 1 will find most application with regard to human deodorants to mask bodily odours. In such circumstances the thickness X of the combination of the barrier layer 3, with the reservoir layer 2 and impermeable layer 4 should be only in the order of a few millimetres and generally less than 5 mm and preferably less than 3 mm so that the patch 1 is not too intrusive to a user. Nevertheless, it will be appreciated that most of this thickness is provided by the central portion comprising the reservoir layer 2 and barrier layer 3 whilst the expansive exposed surface area 10 provided by the permeable layer 4 thereabout acts a "radiator" for the olfactory.

As was described earlier it is important to ensure that the rate of release of the olfactory is controlled and regulated. Generally, the permeable layer 4 will have a steady saturated diffusion rate for olfactory flow laterally and radially away from the well 6 to the expansive areas 10 of the permeable layer 4. In accordance with the present patch 1 the olfactory passes through the preferred pathway defined between the impermeable bottom surface 8 of the reservoir layer 2 and at least surface 9 directly below the layer 2 in order that in this portion of the permeable layer 4 the olfactory can only radiate laterally outwards to the expansive areas 10 for release. Nevertheless, it will be understood that the whole or a more significant proportion of the bottom surface 11 of the layer 2 may be sealed with an impermeable layer again to ensure that release of the olfactory is radially outward and so avoiding the possibility of such olfactory being absorbed by a human beings skin or otherwise.

A patch in accordance with the present invention will generally be adhered to a surface. This surface as indicated may be an area of human skin, but it will be understood that the patch may be used in other situations. Thus, for example a patch may be secured by an adhesive to a garment such as a t-shirt, underwear or socks as well as footwear. In addition to being secured by an adhesive it will be understood that the patch may be secured in an appropriate pocket or secured by a hook fastener or otherwise provided the expansive area of the permeable layer is available for release of the olfactory. The patch could also be sewn or clipped or otherwise associated with a garment.

Typically, the permeable area 4 will comprises a paper or non woven fabric. Generally, to reduce cost the permeable layer may be formed from a filter paper type material whereby olfactories can be drawn from the well 6 for release in the expansive exposed areas 10. In order to indicate when the well 6 is exhausted it may be that a dye of a distinct colour diffuses through the permeable layer 10 under chromatographic conditions in order to indicate in the expansive area 10 that the amount of olfactory in the well has reduced to an unacceptable level for olfactory release. In such circumstances the patch 1 may be replaced or replenished as described later.

The olfactory held within the well 6 as indicated may be a simple perfume or chemically active component such as a mosquito repellent or pleasant smell indicative of a desired odour. In any event, the olfactory released will achieve a particular objective on release. Thus, as indicated for a human being this may be simply to mask a body odour, but as indicated with regard to mosquito repellent, the clear objective is deterring mosquitoes attacking the human being so the two may be combined for dual effect. With respect to further uses it will be understood that a patch in accordance with the present invention could be adhered to packaging for a particular product such as bread so that the olfactory scent is reminiscent of freshly baked bread or with regard to coffee freshly brewed coffee etc. The patch may also be supplied to cinema goers to provide a smell reminiscent of the principal scenes in a film to further stimulate sensory perception. Furthermore, as the radial pathway regulates flow it will be understood that there may be rudimentary time release of individual olfactories at set times after initial activation.

With regard to insect repellents and other agents, it will be appreciated one of the disadvantages of standard skin applications of such a product is that they can be absorbed by the human body and therefore have potential side effects. It will be understood that cream or gel type insect repellents and mosquito repellents are generally rubbed with a deodorant or sun tan lotion directly upon a users' skin. The present patch allows release of insect repellents and mosquito repellents through the porous layer without direct contact between the repellent and the human body and therefore the potential for absorption is eliminated, or at least reduced. It will also be understood that in such circumstances more appropriate and concentrated formulations can be used for repellent actions as the potential for dangerous side effects is reduced through eliminating and limiting the dermatological absorption of this repellent.

A patch in accordance with the present invention may also be incorporated within a mask. These masks may be for household use, hospital surgical masks, DIY masks or heavy machinery masks. In any event the olfactory patch encourages the user to use the mask in comparison with previous masks which may become stale rapidly and provide no incentive for the user to wear the mask. In such circumstances, masks may become more acceptable to users and therefore provide protection when required or will be more acceptable for casual use such as in situations where there may be potential for disease transmission in crowds, such as on a train during winter months or simply through smog and pollution within a town.

It will be understood that in view of the relatively low cost of olfactory patches in accordance with the present invention, a wide range of different concentrations of olfactory within the patch to suit personal preference, length of life of the olfactory, thickness of olfactory use and otherwise may be provided and purchased upon a colour co-ordinated basis for particular customer choice.

As can be seen the well is generally conical or funnel shaped in order to maximise olfactory retention within the well 6 whilst controlling the contact area of the opening 7 with the permeable layer 4.

Generally the present patch 1 will be sufficiently cheaply manufactured in order that the patch 1 is disposed of once exhausted. It will be understood that the barrier layer 3 may simply be a layer of rubber or plastic material thinly applied to cover the reservoir layer and close the well 6. In terms of manufacture a sheet of material from which the reservoir layer 2 is formed may be moulded or shaped with holes created by a moulding tool for the well 6 and the barrier layer 3 then secured upon the top of the respective layer 2. If a reservoir matrix is secured in the well 6 this may occur at the same time as locating the film 3 upon the layer 2. The combination may then be presented to a permeable layer 4 which is screen printed or otherwise with adhesive for engagement against the lower surface 8 of the layer 2. Thus in order to form the patch 1 the patch 1 will be cut with an appropriate press tool to the size of the expansive area 10. The un-adhered portions of the combination of the barrier layer 3 and reservoir layer 2 will then be removed from the sheet by a lifting operation exposing the patches. As indicated generally the bottom of the permeable layer 4 will be made adhesive for securing to a human being or otherwise.

Figure 2:
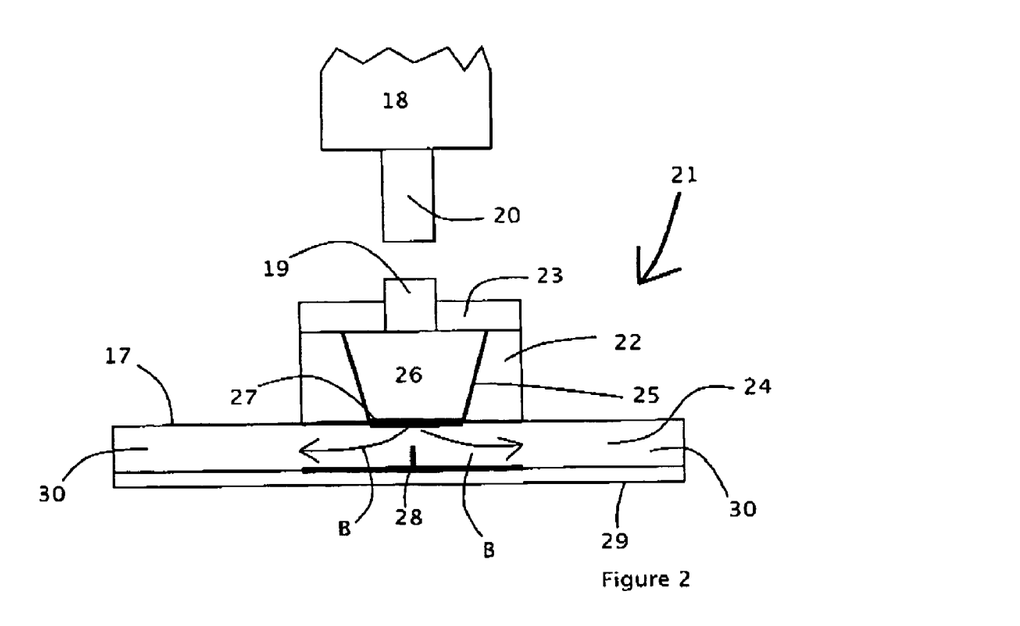
FIG. 2 is a schematic cross section of an olfactory patch in accordance with a second embodiment of the present invention.

If desirable as illustrated in FIG. 2 a barrier layer 23 may include a gland 19 to receive a nozzle 20 so that a well 26 can be refilled. As previously, the barrier layer 23 is secured upon a reservoir layer 22 which in turn is secured upon a permeable layer 24. In use the olfactory flows in the direction of arrowheads B through the permeable layer 24 to expansive areas 30 for release. As previously a bottom layer 29 may act to provide adhesion for the patch 21 as well as define the preferable path through which the olfactory flows in the direction of arrowheads B. A membrane 27 lines the opening of the well and it can be broken when a pin 28 attached to the internal surface of the lower layer of the patch is brought into proximity of the membrane 27 by twisting or squeezing.

It will be understood that the nozzle 20 will be reciprocally shaped with the gland 19 in order that a coupling can be made for release of fluid from a vessel such as a squeezable bottle 18 into the well 26.

The well 26 as previously defined will be a recess 25 in the reservoir layer 22. The well 26 and the surface 25 of the barrier 22 will be impermeable to the olfactory such that the well 26 may be repeatedly refilled with olfactory to allow repeated use of the patch 21.

As an alternative to providing a gland or coupling 19 it will be appreciated that the barrier layer 23 may be rendered auto sealable. Thus, if the barrier layer 23 is formed from an appropriate rubber or plastics material matrix, a needle may be injected into the well 26 in order to fill it with olfactory material and once the needle is removed the elasticity in the barrier layer 23 is sufficiently robust to close across the aperture created by penetration with the needle to ensure closure in the barrier layer 23 to allow further operation of the patch 21. Nevertheless, it will be appreciated that although the patch 21 in such circumstances may be repeatedly used by refilling through a needle penetrating the barrier layer 23, eventually the barrier layer 23 will have so many needle penetrations that it will not be able to prevent leakage of olfactory through the barrier layer 23.

As indicated above generally the well 6, 26 may be filled with a reservoir matrix such as cotton wool or non woven fabric or foam/sponge or be an open void within which normally an olfactory liquid would be located. The volume of the well 26 will be relatively low and sustained release of the olfactory regulated by the preferred path length below the reservoir layer 2 upon the permeable layer 4. In such circumstances generally a single type of olfactory may be used but this may not be acceptable for all situations.

Figure 3:
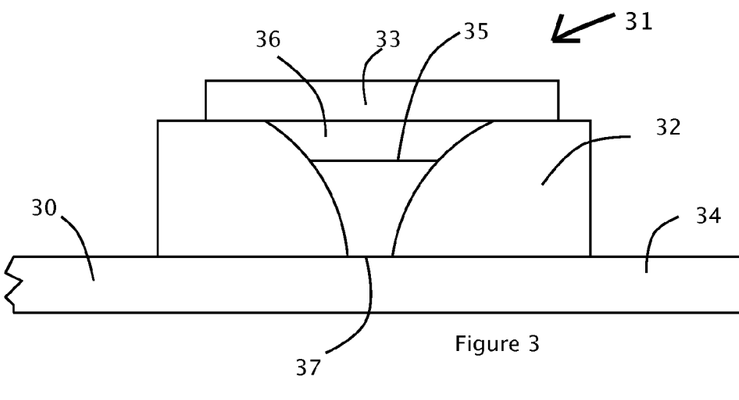
FIG. 3 is a schematic cross section illustrating a well within a patch in accordance with the present invention.

FIG. 3 illustrates a part cross-section of a patch 31 in which a well 36 is formed between a barrier layer 33, a reservoir layer 32 and a permeable layer 34. As previously the well 36 contains an olfactory and is arranged to release the olfactory through an opening 37 so that there is a preferred path beneath the reservoir layer 32 for release in expansive areas 30 round about the reservoir layer 32. As indicated above generally olfactories will be liquids and so will radially pass through diffusion along the permeable layer 34 for release through the expansion areas 30. In the embodiment depicted in FIG. 3 a membrane 35 is provided to divide the well 36 such that prior to first use of the patch 31 two components or types of the olfactory can be separated by the membrane 35. In such circumstances potentially more potent olfactories can be used which may be too intense when combined for storage purposes. Alternatively, a lower portion of the well 36 may be filled with a more concentrated olfactory or gel like olfactory whilst the upper compartment defined by the membrane 36 is filled with a carrier fluid to stimulate release from the gel or dilute the concentration. Upon first use of the patch 31 the barrier membrane 35 will be ruptured mixing the components in the divided parts of the well 36 for radial movement along the permeable layer 34 for release in the expansive areas 30.

Figure 4:
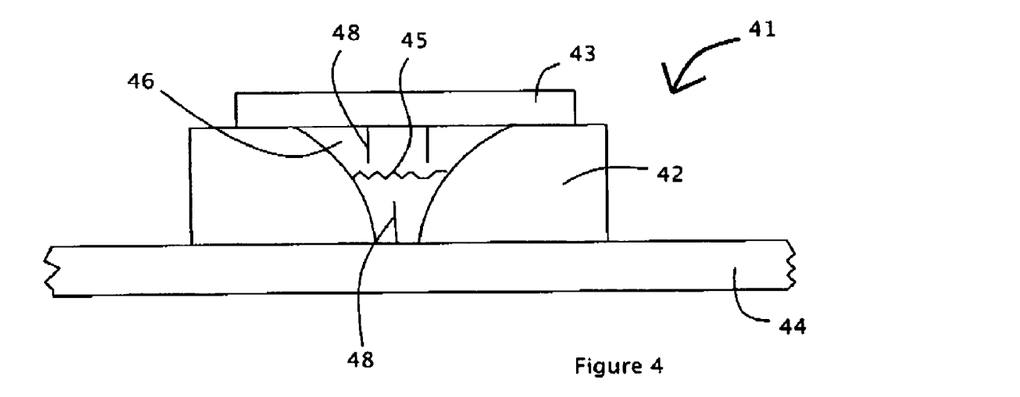
FIG. 4 is a schematic cross section of an alternative well in accordance with the present invention.

It will be appreciated in some circumstances rupture of the membrane 35 through bending or twisting of the patch or simple compression of the barrier layer 33 may be difficult to achieve by normal tactile compression. In such circumstances as depicted in FIG. 4 rupture initiator spikes or other features may be provided in one or both of the compartments formed by a membrane 45 so that it is easier to rupture that membrane 45. Thus, the barrier layer 43 again defines a well 46 with the reservoir layer 42 and permeable layer 44. Thus this well 46 incorporates an olfactory and the membrane 45 prevents mixing of the constituents. Upon first use of the patch 41 the barrier layer 43 is depressed in order that spikes 48 penetrate the membrane 45 to rupture it and cause mixing of the constituents in the well 46. These olfactory constituents then cross through to the permeable layer 44 for release as described above.

As indicated above, spikes or otherwise may be utilised in order to stimulate olfactory release in the patch. Furthermore, as illustrated in FIG. 1, spikes 13 may penetrate an impermeable membrane 12, releasing the olfactory into the permeable layer. It will also be understood that natural compression and squeezing of the patch may be utilised in order to stimulate olfactory flow. Such stimulated olfactory flow will, in such circumstances, enhance the amount of olfactory released.

It will be understood that as indicated previously, olfactory fluid should not generally come into contact with a users' skin surface. In such circumstances generally as described a lower surface of the permeable layer will be adhesive and will be impermeable to prevent the user getting wet.

The olfactory patch may incorporate pores or holes to allow olfactory to dissipate as required. These pores or holes may act to regulate through the available cross section area rate of release of olfactory.

Figure 5:
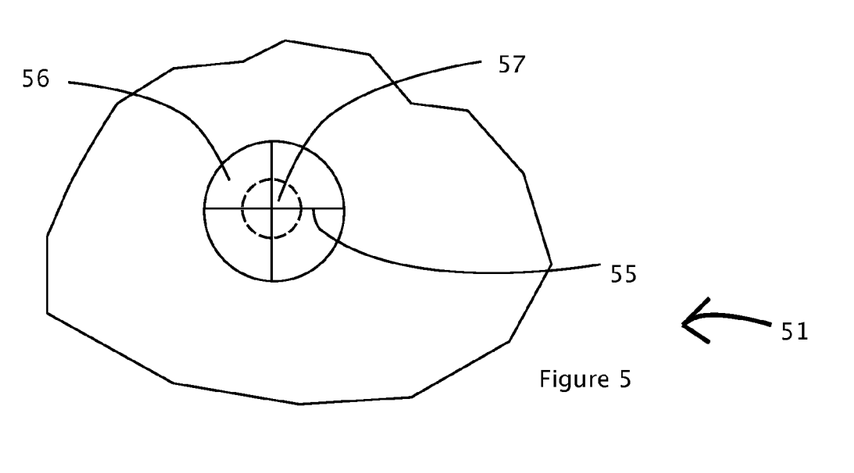
FIG. 5 is a schematic plan view of a well in accordance with a further alternative in accordance with the present invention; and, FIG. 6 provides illustrations of applications of olfactory patches in accordance with the present invention.

Both the arrangements described in FIGS. 3 and 4 essentially divide a well vertically with the membrane 35, 45 extending laterally across the well in order to divide it into two compartments one upon the other. Alternatively, it will be appreciated that a well may be divided laterally to allow two or more constituents to be mixed with each other. Thus, as depicted in FIG. 5 showing a schematic portion of a patch 51 in accordance with the present invention it will be understood that a membrane 55 is provided to divide a well 56 into four quadrants. Each of these quadrants may comprise a constituent for the olfactory when the membrane 55 is broken and the constituents mixed in an outlet 57 shown in broken line. Alternatively, each quadrant may be individually depressed in order to break a membrane for release of that olfactory constituent to the outlet 57 in turn as required by a user.

By dividing the well it will be understood that it will be possible to use different materials or different types of solutions to use the differential diffusion capacity of those different materials or solutions for regulating olfactory release.

Figure 6:
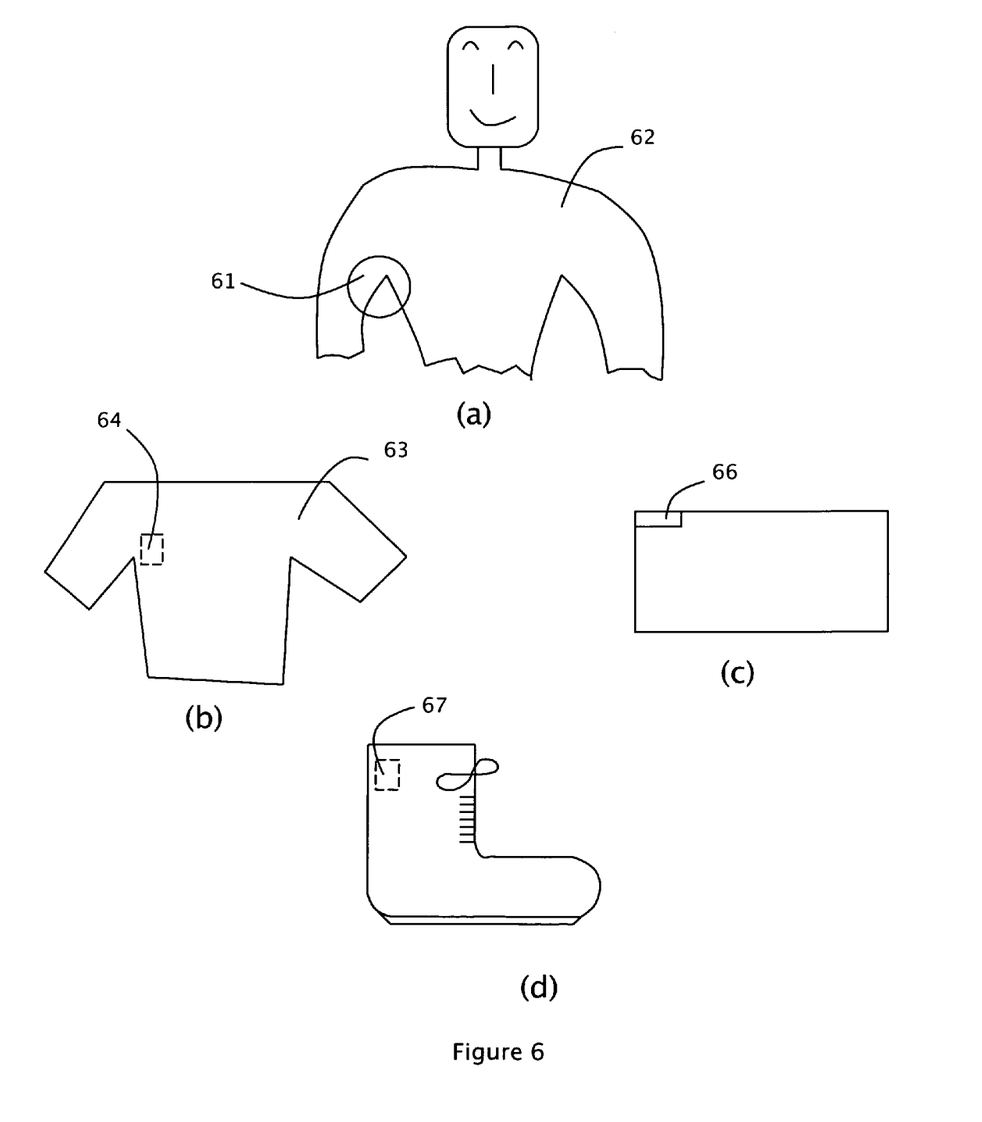

As indicated above patches in accordance with the present invention may be utilised in a number of situations. A few examples of such situations are shown in FIG. 6.

In FIG. 6a the principal use of an olfactory patch in accordance with the present invention is depicted. The olfactory patch will be secured in an armpit 61 of a human being 62 so that the olfactory smell masks the human beings 62 body odour. It will be appreciated that the patch 61 in such circumstances will include an adhesive to allow the patch to be secured in a similar fashion to a first aid plaster to the skin of the user 62. It will be understood that patches could also be secured to other areas of the user 62 which may generate body odours or with regard to patients who have colostomy bag near to that bag.

FIG. 6b illustrates that patches in accordance with the present invention may be secured to appropriate parts of a garment such as a t-shirt 63 or surgical garment. A patch 64 may be positioned in an appropriate pocket or secured upon that t-shirt 61 in order to provide an olfactory again at locations typically where body odours emanate.

In view of the ease with which patches in accordance with the present invention can be secured it will be understood that a further use of patches is illustrated in FIG. 6c where packaging for a food product such as bread, coffee or a fruit such as strawberries has a patch 66 in accordance with the present invention secured to it. In such circumstances the olfactory smell released by the patch 66 will relate to the product within the package, that is to say fresh bread or a smell to enhance the freshness of the strawberries. It will also be understood that a patch may be associated with a storage box or racking or cover such as a suit holder to give a pleasant smell when accessing the stored item.

It will be understood that the patch in accordance with the present invention may be located in footwear and in particular boots or the ankle portion of socks as depicted in FIG. 6d in order to again provide an olfactory smell which masks a body or other odour. As can be seen in FIG. 6d, typically the patch 67 will be secured to an ankle portion of the footwear so that the olfactory and in particular the expansive area for release of the olfactory smell can be appropriately presented. Nevertheless, it will be understood that a patch could be secured at other positions on the sock.

The present olfactory patch comprises a central reservoir or well of olfactory fluid or otherwise which is then spread over a much larger expansive area to facilitate greater olfactory smell release in order to mask other smells or provide a desired cognitive smell for an emulated product or situation. In comparison with previous simpler impregnated patches it will be understood that the rate of release of the olfactory is controlled by the preferential radial path created when the reservoir layer and the permeable layer are secured upon a surface. In such circumstances the operational life of the patch will be extended or at least controlled. Furthermore, the olfactory patch may be refilled as indicated so that the well is replenished with olfactory fluid as required.

In addition to presenting the patch in a pocket or by adhesion to a surface, a further alternative is to provide a housing or pod having a recess into which a patch can be secured. Thus, the patch still has a well and expansion surface formed by a permeable layer which lays against the recess for release of olfactory as required. As indicated heat can cause vaporisation of the olfactory so the housing or pod may have a battery powered heater to stimulate release of olfactory. Furthermore, a small electronic or mechanical pump may be provided to at least regulate olfactory movement along the permeable layer as the preferred radial path to the empty expansion surfaces thereabout.

In addition to the above, it will be understood that an olfactory patch assembly could be made by a stack of patches or wells as described above.

As indicated above, the present olfactory patch can depend upon some form of stimulation or pulse release of a perfume or other olfactory agent. In such circumstances, it will be understood that the olfactory mechanism of the present patch may be applied to a hot plate or other thermal generating mechanism, such as a radiator. Thus the patch will utilize the energy generated elsewhere to help cause diffusion of the olfactory. The released olfactory will then disseminate in areas adjacent to the thermal generating mechanism in order to provide a desired smell or release of mosquito or other repellant agent. It will also be understood that the rate of enhancement of olfactory or other released material will be dependent upon the temperature of the thermal generating mechanism such that there is an auto adjustment and synchronicity with the heat generating system.

The present olfactory patch as indicated will generally create a vapour such that this vapour could be used to avoid humidity in situations where required. Thus, persons who have a breathing difficulty in dry warm environments may be assisted by patches in accordance with the present invention either associated with themselves in a central chest region, or through association with heat generating radiators etc. Furthermore, medical vapours could also be disseminated through patches in accordance with the present invention.

It will be appreciated that air conditioning systems may also provide means for regulating and altering the olfactory flow within a patch in accordance with the present invention.

It will be understood that patches in accordance with the present invention may also be associated with greeting cards and books or other products which may be enhanced by acquiring a scent.

Patches in accordance with the present invention may also be incorporated into a fake flower or in order to enhance the scent from real flowers. The patch may be secured to the flower directly. With regard to fake flowers, it will be understood that the patch may be formed as the central core about petals. Thus the centre of the fake flowers will provide the well in accordance with the present invention with the expansive areas either also provided at a central element of the fake flower, or the petals surrounding the central core of the fake flower acting as the expansive areas from which the scent is radiated. It will also be understood that the well within the patch may be supplied through a stem in the fake flower from a base pot within which the fake flower is secured. The pot including a volume of olfactory which is drawn through capillary or other action into the patch for release in the expansive areas.

It will be understood that where olfactory patches in accordance with the present invention are associated with clothing, that this clothing may only cover a proportion of a wearers' body. In such circumstances the patches will be placed out of view within appropriate pockets of bras/bikinis or otherwise.

Patches in accordance with the present invention may be utilized to freshen up communally used equipment and apparatus. Thus, airline flights and vehicle transports may have patches associated with seats, headrest or eyeshades, such that the aroma released from the olfactory patch enhances the comfort of a user of that seating or otherwise. It will be understood that certain scents may be associated with a user or there may be co-ordination of olfactory scents released by patches from a central register of olfactory sources.

Patches in accordance with the present invention may also be associated with clothing accessories such as clips, waistbands, stickers on clothing and tattoos. It will also be understood that the patches may be an integral feature of a t-shirt design and therefore have a bespoke position within that t-shirt. Nevertheless, such olfactory patches may be removed in order to change the t-shirt design or simply the deodorant used.

Olfactory patches in accordance with the present invention may be incorporated within first-aid boxes such that the scent released from the olfactory patch may be utilised to distract an injured person or provide them with comfort. Furthermore, the olfactory patches may create a disinfectant effect.

Olfactory patches in accordance with the present invention may be associated with electronic instruments. In such circumstances the electronic instrument may be arranged to release a signal or vibration in order to stimulate olfactory flow in the olfactory patch.

The olfactory patch in accordance with the present invention may release a decongestant for a user comprising a mixture of olfactories presented in the well of the olfactory patches described above.

Olfactory patches in accordance with the present invention may be incorporated within a pillow for a user. In such circumstances different aromas may be released at evening time when a user wishes to fall asleep, and morning time when they wish to wake up to a fresh morning smell.

Generally, as indicated the permeable layer will be formed from a paper matrix. However, it will be understood that other matrixes can be utilized including foam and plastics materials.

As indicated the olfactory held within the well may be in the form of a liquid or a gel. The viscosity of the olfactory within the well may be adjusted in order to alter the rate of olfactory flow from the well to the periphery of the permeable layer for release of the olfactory into the environment.

Olfactory patches as indicated can be associated with garments for personal choice or work wear such as surgical shirts and garments to calm patients and others as to the wearers of those garments.

As indicated above generally the side of the wells, holes and general shaping of the olfactory patch will be dependent upon user requirements.

Possibly, patches in accordance with the present invention may be formed from biodegradable material or natural material such as wood.

The olfactory patch may be secured to a base with flaps. The base includes apertures for release of perfume. Thus, the patch may be selectively secured to a base by displacing the flaps.

The olfactory patch could be part of a bandage or plaster or other dressing for a wound. The patch may be embedded or simply secured to the dressing with the olfactory having medicinal value.

The olfactory patch may be secured to a pen or nappy or waste bin or be part of an adhesive tape or note pad or household utensil.

It will also be understood that the patch may include an absorption layer formed from foam or the like to absorb perspiration etc.

Thus the reader will see that the olfactory patch provides a highly effective, yet economical device for the dissemination of olfactory such as fragrance, deodorizing agents or other odors.

It will be understood that patches in accordance with the present invention may also be used to deliver therapeutic agents, to be delivered topically or to be inhaled. This is particularly useful in the area of sustained release of pharmacologically active compounds such as anti-addiction drugs used by those fighting nicotine or other drug addictions. Also another useful function of these patches would be to provide pain relief topically at the site of the problem. Further, could provide the use of other drugs to specific parts of the body utilizing the patch system.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

While my above description contains many specifications, these should not be construed as limitations on the scope of the invention, but rather as an exemplification of the preferred embodiment thereof. Many other variations have been described, but using the same novel principles other embodiments are possible. Accordingly, the scope of the invention should be determined not by the embodiments illustrated, but by the appended claims and their legal equivalents.

The invention claimed is:

1. What is claimed is an olfactory patch which comprises a well formed by a reservoir layer, the well being sandwiched between a barrier layer on a top side and a permeable layer on a bottom side and containing an olfactory fluid, an impermeable membrane interposed between said bottom side of the well and said permeable layer such that upon triggering an initiator mechanism, said impermeable membrane is breached allowing the olfactory fluid to leave the well and enter the permeable layer.

2. The olfactory patch as claimed in claim 1, wherein the permeable layer comprises a paper matrix having the consistency of filter paper.

3. The olfactory patch as claimed in claim 1, wherein the olfactory fluid comprises at least one of a perfume, a deodorant, an insect repellant and a medicinal agent.

4. The olfactory patch as claimed in claim 1, wherein said well is filled with a reservoir matrix or the well is an open void within which the olfactory liquid is contained.

5. The olfactory patch as claimed in claim 1, wherein the well is compartmentalised or shaped to allow controlled release of the olfactory fluid from the well.

6. The olfactory patch as claimed in claim 1 wherein the well is filled with different compositions for regulating olfactory release.

7. The olfactory patch as claimed in claim 1 wherein the well is penetrable to fill the well with an olfactory fluid.

8. The olfactory patch as claimed in claim 1 further comprising a pathway for the olfactory fluid through the permeable layer in a direction that is radial, vertical or lateral.

9. The olfactory patch as claimed in claim 1 wherein the olfactory fluid spreads by diffusion from a high concentration within the reservoir layer to a lower concentration within the permeable layer.

10. The olfactory patch as claimed in claim 1 wherein the olfactory fluid radiates or is convectively released from the permeable layer thus providing a gradient of flow of olfactory fluid from the reservoir layer to the permeable layer.

11. The olfactory patch as claimed in claim 1 wherein the olfactory fluid has medicinal value that is delivered to the user through the inhalation of the aromatization of the olfactory fluid or via direct absorption through the skin surface of the user.

12. The olfactory patch as claimed in claim 1 wherein the initiator mechanism comprises a pin or a spike.

13. The olfactory patch as claimed in claim 1 further comprising a thermal generating mechanism, either internally or externally, to enhance olfactory fluid flow from the well to the permeable layer.

14. The olfactory patch as claimed in claim 13, wherein the thermal generating mechanism further comprises a battery powered heater to stimulate release of the olfactory fluid.

15. The olfactory patch as claimed in claim 1 comprising a small electronic or mechanical pump to regulate olfactory fluid flow across the patch to an area external to the olfactory patch.

16. The olfactory patch as claimed in claim 1 wherein the initiator mechanism breaches the impermeable membrane when pressure is applied, releasing olfactory fluid into the permeable layer.

17. The olfactory patch as claimed in claim 1, further comprising an attachment means disposed thereon for attaching the patch to any surface.

18. The olfactory patch as claimed in claim 1, wherein the initiator mechanism is triggered by either a pin-like process, or by a bending or twisting of the olfactory patch.

19. An olfactory patch comprising:
a barrier layer; a permeable layer; a reservoir layer sandwiched between the barrier layer and the permeable layer, said reservoir layer forming a well between the barrier layer and the permeable layer; an impermeable membrane lining the well for receiving an olfactory fluid; and an initiator mechanism for breaching the impermeable membrane and permitting the olfactory fluid to enter the permeable layer.

20. The olfactory patch of claim 19, wherein the barrier layer houses a valve for refilling the well with olfactory fluid.

* * * * *